United States Patent [19]

Goodwin et al.

[11] Patent Number: 4,863,713

[45] Date of Patent: Sep. 5, 1989

[54] METHOD AND SYSTEM FOR ADMINISTERING THERAPEUTIC AND DIAGNOSTIC AGENTS

[75] Inventors: David A. Goodwin, Atherton; Claude Meares, Davis; Michael McCall, Vacaville, all of Calif.

[73] Assignee: The Board of Trustees of Leland Stanford Jr. Univ., Stanford, Calif.

[21] Appl. No.: 877,327

[22] Filed: Jun. 23, 1986

[51] Int. Cl.[4] .................... A61K 49/02; A61K 49/00; C07F 13/00

[52] U.S. Cl. ........................................ 424/1.1; 424/9; 534/14

[58] Field of Search ....................... 424/1.1, 9; 534/14

[56] References Cited

U.S. PATENT DOCUMENTS

| | | | |
|---|---|---|---|
| 3,935,074 | 1/1976 | Rubenstein et al. | 424/1.1 X |
| 3,994,966 | 11/1976 | Sundberg et al. | |
| 4,043,998 | 8/1977 | Meares et al. | |
| 4,130,462 | 12/1978 | Rubenstein et al. | 424/1.1 X |
| 4,339,426 | 7/1982 | Meares et al. | 424/1.1 |
| 4,478,815 | 10/1984 | Burchiel et al. | 424/1.1 |
| 4,624,846 | 11/1986 | Goldenberg | 424/1.1 |
| 4,634,586 | 1/1987 | Goodwin et al. | 424/1.1 |
| 4,699,877 | 10/1987 | Cline et al. | 424/1.1 X |
| 4,741,900 | 5/1988 | Alvarez et al. | 424/1.1 X |

OTHER PUBLICATIONS

Chien-Hsing Chang, Jerry L. Dallas, and Claude F. Meares, Identification of a Key Structural Feature of Cobalt(III)-Bleomycins: An Exogenous Ligand (e.g. Hydroperoxide) Bound to Cobalt, vol. 110, No. 3, 1983, Feb. 10, 1983, BPSR, pp. 959–966, by Academic Press, Inc., 0006-291X/83/030959.

Leslie H. DeRiemer, Claude F. Meares; Dept. of Chemistry, UC Davis, Calif. 95616, David A. Goodwin & Carol I. Iamanti; Stanford University School of Med., Calif. 94304, Bledta II: Synthesis of a New Tumor-Visualizing Derivative of Co(III)-Bleomycin, Jrnl. of Labelled Compounds & Radiopharmaceuticals-vol. XVIII, No. 10, Wiley & Sons, '80.

D. A. Goodwin, C. F. Meares, C. I. Diamanti & M. W. Sundberg, (Stanford U.), Biofunctional Chelates for Radio-Pharmaceutical Labeling, pp. 363–373, Work supported by NIH(GM14752), the NSF(G.P.-4924), the Calif. Div. of the American Cancer Society (#685) and the U.S. Veterans Administration (#3204).

Clinical Studies with In-111 Bledta, A Tumor-Imaging Conjungate of Bleomycin, David A. Goodwin, Claude F. Meares, Leslie H. DeRiemer, Carol I. Diamanti, Richard L. Good, John E. Baumert, Jr., David J. Sartoris, Robert L. Lantieri, & H. Daniel Fawcett. VAMC & Stanford U. of Med. in Palo Alto, Calif. & UC Davis, Calif., Reprinted from the Journal of Nuclear Medicine, 9/81, vol. 22, #9.

Goodwin, Meares, Diamanti, McCall, Lai, Torti, McTigue, and Martin, Use of Specific Antibody for Rapid Clearance of Circulating Blood Background from Radiolabeled Tumor Imaging Proteins* Supported in part by VAR Grant & PHS Grants, Eur. J. Nucl. Med., (1984), 9:209–215, in European Journal of Nuclear Medicine, Springer-Verlag, '84.

(List continued on next page.)

*Primary Examiner*—John S. Maples
*Attorney, Agent, or Firm*—Peter J. Dehlinger

[57] ABSTRACT

A method and system for localizing a diagnostic or therapeutic agent to an internal target site. The system includes (1) an epitopic compound, (2) a binding protein which is effective to bind specifically with the compound and capable of localizing selectively at the target tissue, when administered parenterally, and (3) a clearing agent which can bind to and cross-link the binding protein, to form a protein aggregate which is readily cleared from the subject's bloodstream. In practicing the method of the invention, the binding protein is administered to the subject parenterally, and allowed to localize at the target site, typically within 1–4 days. This is followed by a chase with the clearing agent to remove circulating, but not target-localized binding protein. When the epitopic compound is administered, binding of the compound to the localized binding protein, and rapid clearance of unbound compound by the kidneys, results in selective localization of the compound at the target site.

20 Claims, 1 Drawing Sheet

OTHER PUBLICATIONS

Meares, Goodwin, Leung, Girgis, Silvester, Nunn, and Lavender, Covalent Attachment of Metal Chelates to Proteins: The Stability In Vivo and In Vitro of the Conjugate of Albumin with a Chelate of Indium, Proc. Natl. Acad. Sci., U.S.A., 73, (1976), pp. 3803–3806, Reprint, vol. 73, No. 11, Nov. 1976, Chemistry.

Meares, McCall, Reardan, Goodwin, Diamanti, and McTigue, Conjugation of Antibodies with Bifunctional Chelating Agents: Isothiocyanate and Bromoacetamide Reagents, Methods of Analysis, and Subsequent Addition of Metal Ions, In Analytical Biochemistry, 142, 68–78, (1984), 0003-2697/84 $3.00, pp. 68–78.

Sundberg, Meares, Goodwin, and Diamanti, Selective Binding of Metal Ions to Macromolecules Using Bifunctional Analogs of EDTA, Reprint from the Journal of Medicinal Chemistry, 17, 1304, (1974), Copyright 1974, by the American Chemical Society, 4 pgs., Journal of Medical Chemistry, 1974, vol. 17, No. 12.

Simon M. Yeh, David G. Sherman, and Claude F. Meares., Dept. of Chemistry, UC Davis, Calif. 95616, A New Route to "Bifunctional" Chelating Agents: Conversion of Amino Acids to Analogs of Ethylenedinitrilotetraacetic Acid, Analytical Biochemistry, 100, 152–159, (1979), Copyright Academic Press, Inc.

S. M. Yeh, C. F. Meares and D. A. Goodwin, U.C. Davis, Stanford School of Medicine and VAMC in Calif., U.S.A., Decomposition Rates of Radiopharmaceutical Indium Chelates in Serum, in Journal of Radioanalytical Chemistry, vol. 53, No. 1–2, (1979), 327–336.

Sundberg, Meares, Goodwin and Diamanti, Chelating agents for the Binding of Metal Ions to Macromolecules, in Reprinted from Nature, vol. 250, No. 5467, pp. 587–588, Aug. 16, 1974), Revised May 2, 1974.

Scott W. Burchiel, Ph.D. and Buck A. Rhodes, Ph.D., Radioimmunoimaging and Radioimmunotherapy, Elsevier, N.Y., *Amsterdam* Oxford, 1983, by Elsevier, "Bifunctional" Chelating Atents for Binding Metal Ions to Proteins by Wengel & Meares, 12 pgs.

Reardan, Meares, Goodwin, McTigue, David, Stone, Leung, Bartholomew, and Frincke, Antibodies Against Metal Chelates, Macmillan Journals, Ltd., 1985, 3 pgs, accepted May 12, 1985.

Michael William Sundberg, Aug. 1983, A Dissertation Submitted to the Dept. of Chemistry and the Commiutee on Graduate Studies of Stanford University in Partial Fulfillment of the Requirements for the Degree of Doctor of Philosophy, "Bifunctional EDTA Analogues with Applications for the Labeling of Biological Molecules", 164 pgs.

DeRiemer, Mearres, Goodwin & Diamanti, Articles, Bledta: Tumor Localization by a Bleomycin Analogue Containing a Metal–Chelating Group, in Journal of Medicinal Chemistry, 1979, by American Chemical Society vol. 22, No. 9, Sep. 1979, 5 pgs., 0022-2623/79/1822-1019$1.00/0.

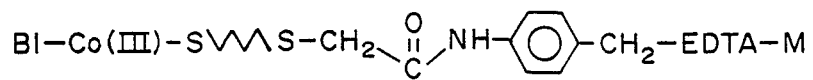
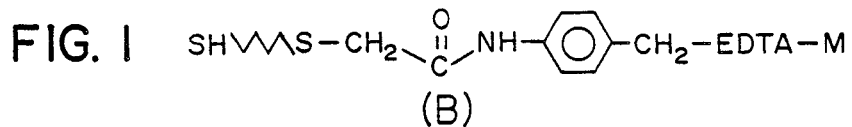
FIG. 1
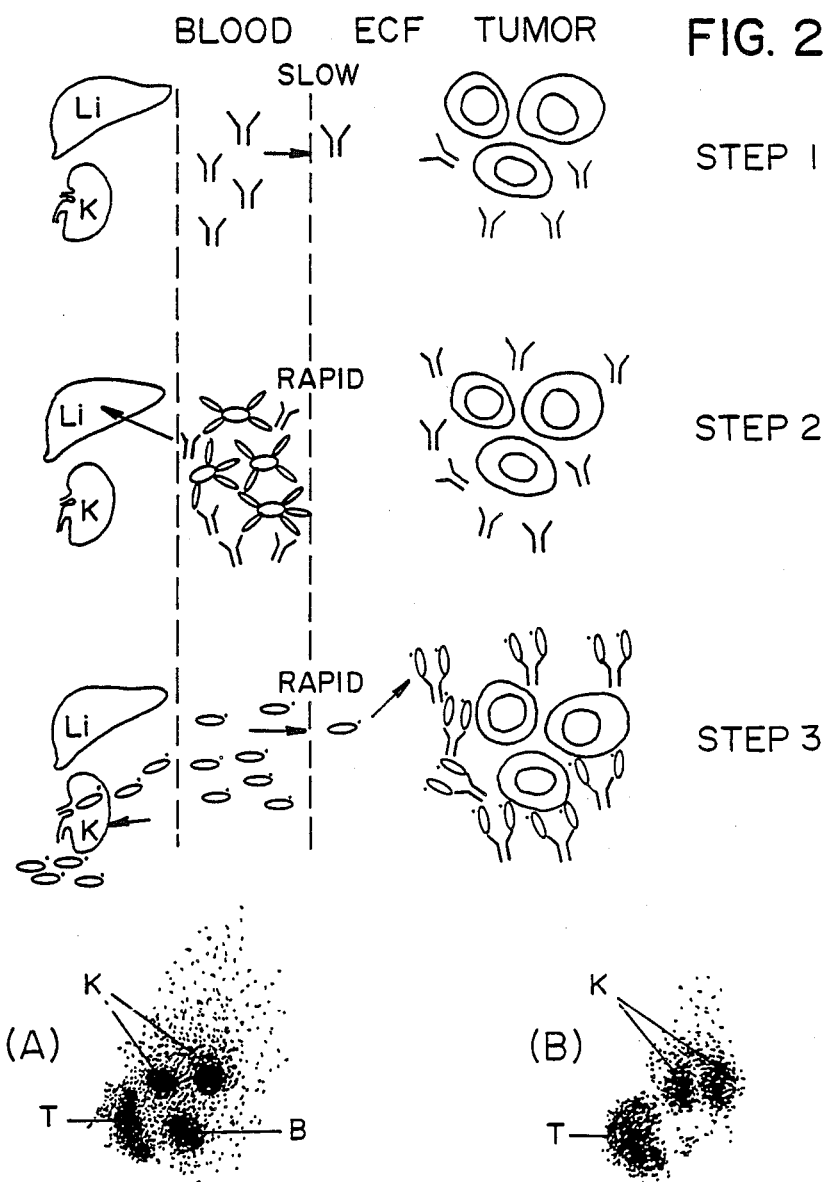
FIG. 2
FIG. 3

METHOD AND SYSTEM FOR ADMINISTERING THERAPEUTIC AND DIAGNOSTIC AGENTS

The invention described herein was made in the course of work under contracts from the U.S. National Institutes of Health/NCI Grant Nos. 5 R01 CA28343, CA00462, and CA16861 of the Department of Health and Human Services.

FIELD OF THE INVENTION

The present invention relates to a method and system for administering a therapeutic or diagnostic compound, and in particular, a radionuclide, to produce target-specific localization of the agent.

REFERENCES

Chang, C.-H., et al, *Biochem, Biophys Res Commun* 111 (3): 959 (1983).
De Riemer, L. H., et al, *J Med Chem* 22: 1019 (1979).
De Riemer, L. H., et al, *J Lab Comps & Radpharm* 18 (10): 1517 (1981).
Friguet, B., et al, *J. Immunol Methods* 77: 305 (1985).
Fujii, A. J., *Antibiot* 26: 398 (1973).
Goodwin, D. A., et al, *Nuclear Medizin* 14: 365 (1975).
Goodwin, D. A., et al, *Seminars in Nuc MUD* VI: 3 (1976).
Goodwin, D. A., et al, *In Radiopharmaceuticals II*
Proceedings of the Second International Conference on Rad, N.Y., Sodd, V. J., et al, eds. pp 275–284 (1979).
Goodwin, D. A., et al, *J Nuc Med* 22: (9): 787 (1981).
Goodwin, D. A., eta l, *Eur J Nuc Med* 9: 209 (1984).
Kohler, B., et al, *Nature* 256: 495 (1975).
Meares, C. F., et al, *Proc Natl Acad Sci (USA)* 73 (11): 3803 (1976).
*Monoclonal Antibodies*, Kennett, T. J., et al, eds Plenum (1980).
Umezawa, H., *Pure Appl Chem* 28: 665 (1970).
Wensel, T. G., et al, in *Radioimaging and Radioimmunotherapy*, Burchiel, S. W., et al, eds, Elsevier, p 185 (1983).

BACKGROUND OF THE INVENTION

A major focus of current drug research is to improve drug targeting to internal target sites, such as to solid tumors or specific organs. The objective of drug targeting is to enhance the effectiveness of the drug by concentrating it at the target site, and minimizing its effects in non-target sites. For example, where the drug is used for therapeutic purposes, such as to treat a solid tumor, drug targeting allows more effective dosing at the target site with fewer non-tumor related side effects. Similarly, where the drug agent is a radionuclide for use in radioimaging, targeting gives enhanced contrast between the target and background areas, because of reduced background levels of the radionuclide.

Radionuclides are an important group of pharmaceutical agents for which a variety of targeting strategies have been proposed. Included in this group are radioimaging compounds, such as metal chelates of $^{111}$In, $^{67}$Ga, $^{64}$Cu, $^{99m}$Tc, $^{68}$Ga, $^{62}$Zn, $^{67}$Cu, $^{197}$Hg, $^{97}$Ru, $^{57}$Co, or $^{53}$Co, which are used to image internal sites, particularly solid tumors, by intravenous administration and systemic uptake of the chelates. Also included are radiotherapeutic agents, such as the metal chelates of $^{90}$Y, $^{197}$Hg or $^{67}$CU, or conjugates of other radioactive elements, such as $^{131}$I which are used in treating tumors and the like, based on localized cell destruction from ionizing radiation. A related group of pharmaceutical agents are non-radioactive metal chelates such as iron, copper or ruthenium chelates, which produce cytotoxic effects through redox mechanisms, and can also potentiate the cytotoxic action of radiation on cells.

Previously, the inventors have described several novel chelate compounds which are useful for targeting radionuclides and radiosensitizing metals to internal sites, particularly solid tumors. In general, these compounds are bifunctional chelating agents which have, as one functional group, a chelating moiety capable of forming a tight complex with a metal ion, and as a second functional group, a chemically reactive moiety, such as a nitro or amine group, through which the compound can be coupled to a targeting or other molecule (Meares, 1976; Goodwin et al, 1975, 1976, 1979).

One novel class of chelate compounds which has been developed by the inventors are various ethylenediaminetetraacetic acid (EDTA) chelates of bleomycin, which is an anti-tumor antiobiotic which localizes within many types of tumors (Umezawa, Fujii). The bleomycin/EDTA compounds have been shown to give selective tumor localization of a variety of radionuclides, including $^{57}$Co and $^{111}$In, in solid tumors. One of the earliest of these compounds was prepared by alkylating purified bleomycin A$_2$ with a reactive bifunctional compound, such as p-bromoacetamidobenzyl-EDTA (BABE-EDTA), to link the chelate to bleomycin through a sulfonium group (DeRiemer; Goodwin, 1979, 1981; Chang). A more recent compound, formed by joining a bifunctional EDTA molecule to a bleomycin-Co complex through a monodentate cobalt-sulfur coordinate bond, is described in co-owned U.S. patent application for "Bleomycin Conjugates and Methods", U.S. Pat. No. 4,758,421 issued July 19, 1988.

One of the limitations which has been observed in targeting small radionuclide compounds, such as the above bleomycin/metal chelate compounds, to a target site, such as a solid tumor, is relatively low concentration of the compound at the target site. The low drug dose at the target site is due to the rapid clearance of the compound by the kidneys, which limits the amount the compound in the bloodstream available for localization at the target site. Merely increasing the dose of the administered compound is not a practical solution, since most of the radionuclides are toxic and therefore dose-limiting.

One method for increasing the concentration of a dose-limited, but rapidly cleared, target compound is to coadminister the compound in an antibody-complexed form. Because of its relatively large size, the complex is not cleared by the kidneys, but instead, is removed slowly from the bloodstream over a several day period by the reticuloendothelial system (RES). This approach has been investigated previously by the inventors, using two monoclonal antibodies (Mabs) prepared against the bifunctional indium/chelate compound L-benzyl-EDTA-$^{111}$In (LBEDTA-In). Binding studies showed that both antibodies were specific for the indium chelate, giving K$_b$ values for the indium chelate which were at least about 20 times those of the chelates of other metals. The antibodies, when coadministered with BLEDTA-$^{111}$In, increased the whole body level of BLEDTA-$^{111}$In after 24 hours between 10–30 times, presumably by retaining the BLEDTA-In compound in a tightly bound systemic form which is cleared slowly from the bloodstream.

The increased uptake of the compound in the presence of circulating anti-compound antibodies is, however, a relatively non-specific effect, since a variety of organs which were tested for $^{111}$In levels also showed significantly increased radioactivity after 24 hours. Therefore, the advantage of the enhanced tumor uptake of the compound produced by coadministration of an antibody is partially offset by (1) higher background levels of radioactivity (or a therapeutic agent) in non-tumor organs, and (2), greater total patient exposure to the conjugate, e.g., greater radiation exposure in the case of a conjugate having a chelated radionuclide.

Although it may be possible to reduce these unwanted side effects by flushing the patient's bloodstream with a non-toxic or non-radioactive competing antigen, the improvement in terms of reduced exposure to the compound is not dramatic. Earlier studies conducted by the inventors showed, for example, that whole body BLEDTA-$^{111}$In levels are reduced only about 20% three hours after giving a flushing dose of Fe-EDTA. Further, the antibody-enhancement approach just described requires periods of at least several hours for significant target distribution effects; therefore, the method is not suited for radionuclides such as $^{99m}$Tc and $^{68}$Ga which have half lives of between about one to a few hours.

SUMMARY OF THE INVENTION

It is one general object of the invention to provide, for targeting a therapeutic or radiodiagnostic compound to a target organ, an improved method and system which substantially overcome above-discussed problem and limitations known in the prior art.

It is a more specific object of the invention to provide a method and system for selectively targeting radionuclides to solid tumor areas.

Another object of the invention is to provide such a method and system in which body exposure to high levels or radionuclide or other drug compounds occurs over a short period of time only.

Still another object of the method is to provide such a system and method which are compatible with very short-lived radionuclides, such as $^{68}$Ga.

The invention includes, in one aspect, a method of localizing at an internal target site of a subject, a diagnostic or therapeutic epitopic compound whose size allows rapid clearance by the kidneys. In practicing the method, there is provided a binding protein which is (a) effective to bind specifically and with high affinity to an epitope associated with the compound, and (b) capable of localizing selectively at the target tissue when administered to the subject parenterally. The binding protein is typically an antibody, which is specific against an antigenic epitope associated with the compound, or a non-immunoglobulin binding protein, such as avidin, which has a high binding affinity for a small epitopic moiety, such as biotin.

The binding protein is administered parenterally to a patient, without the associated epitopic compound, and allowed to localize selectively at the target site. After a typically one-to-four day period for localization, non-localized circulating binding protein is removed by parenterally administering a clearing agent capable of reacting with circulating binding protein to form a macromolecular aggregate which can be cleared rapidly by the subject's reticuloendothelial system. The clearing agent typically includes a carrier macromolecule, such as a human serum protein, containing a number of covalently bound epitopic groups. After a period sufficient for removal of most of the aggregate, typically about one hour or less, the epitopic compound is given parenterally, wherein binding of the compound to the localized binding protein, and rapid clearance of unbound compound by the kidneys leads to selective localization of the compound at the target site.

In one embodiment the epitopic compound is an epitope-chelate compound complexed with a metal ion to form a stable metal chelate complex, and the binding protein is an antibody specific against the epitopic moiety of the compound. An exemplary chelate compound is a metal chelate of a 1-phenyl or 1-benzyl EDTA having a parasubstituted spacer arm. The metal may be a radionuclide useful for radioimaging, such as $^{111}$In, $^{67}$Ga, $^{64}$Cu, $^{99m}$Tc, $^{68}$Ga, $^{62}$Zn, $^{67}$Cu, $^{197}$Hg, $^{97}$Ru, $^{57}$Co, or $^{53}$Co; a radionuclide used for tumor therapy, such as $^{90}$Y, $^{197}$Hg or $^{67}$Cu; or a radio-sensitizing chelated metal, such as chelated iron, copper or ruthenium.

The system of the invention includes the epitopic compound containing the agent to be localized and an associated epitopic moiety, and a binding protein (a) effective to bind specifically and with high affinity to an epitope associated with the compound, and (b) capable of localizing selectively at a target site when administered to a subject parenterally. Also included in the system is a clearing agent capable of reacting with the binding protein, wich such circulating in the bloodstream of the subject, to form a macromolecular aggregate which can be cleared rapidly by the subject's reticuloendothelial system.

These and other objects and features of the invention will become more fully apparent when the following detiled description of the invention is read in conjunction with the accompanying drawings.

BRIEF DESCRIPTION OF THE DRAWINGS

FIG. 1 shows the molecular structure of (A) a bleomycin-EDTA-metal chelate and (B) a dithiobutane-EDTA-metal chelate which are exemplary embodiments of epitopic compounds which can be targeted to solid tumor regions by the method of the invention;

FIG. 2 illustrates, in diagrammatic form, the steps by which a therapeutic or radiodiagnostic compound is localized in a tissue, according to the method of the invention; and FIG. 3 shows whole-body photo-emission scans of a tumor-bearing animal 3 hours (A) and 24 hours (B) after administration of a radionuclide-chelate compound, according to the method of the invention.

DETAILED DESCRIPTION OF THE INVENTION

I. Preparing the System Components

A. Epitopic Compounds

The invention is designed for use in targeting a therapeutic or radioimaging agent at a specific internal body site, such as a solid tumor or selected organ or tissue site. The agent which is targeted is part of an epitopic compound having a pharmaceutically active therapeutic or radioimaging moiety or agent (the active moiety), and one or more epitopic, or recognition moieties which can bind specifically and with high affinity to a epitope-specific binding protein.

The active moiety of the compound is a pharmaceutically active agent, such as a drug, radionuclide, hormone, toxin, metabolite, anti-metabolite, vitamin, enzyme-factor, or the like which either contains a natural epitopic moiety, or, in the more usual case, can be modified or derivatized to contain the requisite epitope moiety without loss of activity. Such active agents include anti-tumor agents, as exemplified by doxorubicin, cisplatin, DNA alkylating or cross-linking agents, and antimetabolites; and anti-microbial agents, such as aminoglycosides and polyene and macrolide antibiotics, such as amphotericin B. One major class of therapeutic and diagnostic agents useful in the invention are chelated metals, including chelated radionuclides useful for radioimaging, such as $^{111}$In, $^{67}$Ga, $^{64}$Cu, $^{99m}$Tc, $^{68}$Ga, $^{62}$Zn, $^{67}$Cu, $^{197}$Hg, $^{97}$Ru, $^{57}$Co, or $^{53}$Co; chelated radionuclides useful for tumor therapy, such as $^{90}$Y, $^{197}$Hg or $^{67}$Cu; and a radio-sensitizing chelated metals, such as chelated iron, copper or ruthenium.

The epitopic moiety, which is also referred to herein as an epitope, is the structural portion of the compound which is recognized specifically and with high binding affinity by an anti-epitope binding protein. Among the preferred classes of epitopes herein are haptenic antigens, which are specifically bound by the antibody binding proteins; biotin, which is specifically bound by avidin; and carbohydrates of the type which are bound by plant lectin binding proteins.

The method of the invention requires that the epitopic compound be sufficiently small and soluble when administered parenterally that it can be cleared rapidly from the kidneys. Typically molecules with molecular weights less than about 50,000 daltons, and preferably less than about 10,000 daltons, and which exist predominantly in monomolecular form in serum generally satisfy these requirements.

In the usual case, the epitopic compounds are prepared either by derivatizing the active agent with one or more distinct epitopic groups, such as biotin, or a defined antigen, or by modifying the active agent to produce an antigenic or haptenic moiety against which monoclonal antibodies can be generated. Both modification and derivatization reactions generally follow known methods for derivatizing or modifying compounds at reactive chemical sites, such as carboxyl, amino, nitro, hydroxyl, aldehyde, and sulfhydral sites. These reactions may involve direct alkylation reactions, coupling reactions which proceed through activating agents, such as a carbodiimide, isothiocyanate, or N-hydroxysuccinimide, or coupling through a bifunctional cross-linking agent such as glutaraldehyde. Suitable reactions would be well-known to one skilled in the art, based on the nature of the reactive groups which are available in the active agent, information about the active site requirements of the agent, and the type of chemical modification or epitope addition which is desired. The chemical derivatization and modification reactions described below are illustrative.

One important class of active agents which are useful in the present invention are bifunctional chelate agents. These compounds, which have been reported earlier by the inventors, contain an EDTA or other metal chelation functionality capable of forming a tight metal complex with a variety of pharmaceutically useful metals. The chelate moiety is typically joined through a benzyl ring to a functional reaction group, such as a nitro, amine, or bromoacetomido group, which can be used in coupling the compound to other molecules, such as proteins, bleomycin, or smaller molecules which can form part of the hapten in the derivatized or modified compound. The modification reactions used to produce compounds A and B are illustrative.

Compound A in FIG. 1 is a cobalt/bleomycin (Bl—Co(III)) compound derivatized to a bifunctional EDTA through a stable monodentate CO(III)—S bond. The synthesis of this compound is detailed in the above cited patent application for "Bleomycin Conjugate and Method", which is incorporated herein by reference. Briefly, Bl—CO(III)—H$_2$O is reacted with 1,4-dithiolbutane under conditions which lead to reversible displacement of the cobalt-bound water, and formation of Bl—Co(III)—S—(CH$_2$)$_4$SH. The synthesis is completed by reacting the dithio-bleomycin compound with p-bromoacetomidobenzyl-EDTA (BABE-EDTA), and purification of the derivatized bleomycin compound by high pressure liquid chromatography (HPLC). Here it is noted that the thiobutane spacer arm can be substituted by a variety of carbon-containing chains of varying length and composition, and which terminates at a variety of free-end chemical groups, such as a thiol, amine, carboxyl, or hydroxyl group, by which the chain can be covalently coupled to a bifunctinal chelate. Similarly, the bifunctional chelate can have one of a variety of chemical groups suitable for covalent coupling to spacer-arm free end.

The compound shown at B in FIG. 1 contains the same dithiobutane-BABE-EDTA structure as compound A, but not the Co-linked bleomycin. The compound can be formed by reacting 1,4, dithiobutane directly with BABE-EDTA, as described in Example 1. As will be seen in Section IB below, monoclonal antibodies (Mabs) prepared against the thiobutane-BABE-EDTA-CO antigen are specifically reactive with metal chelates of both compounds A and B. Each compound is thus representative of a pharmaceutical active agent (the BABe-EDTA-metal chelate) which is modified (by addition of a four-carbon thio-linked spacer) to form a hapten which is capable of provoking an antibody response in an immunized animal. The two modification reactions also illustrate generally the principle of drug or chelate coupling reactions in which a spacer arm is used to minimize the effect of modification or addition at the functional portion of the compound.

To illustrate a derivatization reaction used in preparing a epitopic compound, the above bifunctional chelates can be coupled to a biotin moiety, to produce of epitopic biotin chelate capable of specific, high-affinity binding to avidin. In one coupling method, a bifunctional chelate having a free-end amine is reacted with an N-hydroxysuccinamide (NHS) ester of biotin, to link the biotin to the chelate amine through an amide linkage. The chelate amine may be formed from BABE-EDTA, for example, by amination in concentrated aqueous ammonium, and the NHS biotin ester is commercially available. The resulting biotinylated glycineamidobenzyl EDTA (GABE-EDTA) has been shown to bind with high affinity to avidin. Other active agents can be biotinylated or derivatized with carbohydrate or haptenic molecules in a similar manner.

Epitopic compounds containing two or more haptenic epitopes, to give enhanced antibody binding, may be prepared by the same general methods discussed above. In derivatizing an active agent with multiple epitopes, the individual epitopes can be attached to different sites on an active agent, or may be attached at different positions on a single spacer arm attached to the active agent. Where the active agent has been chemically modified to a haptenic form, it is possible to form bivalent species by linking compounds together in dimeric form. For example, compound B in FIG. 1 can be dimerized readily through a disulfide bond, to form a bivalent haptenic species.

B. Binding Proteins

The binding protein in the system of the invention serves both as a targeting agent capable of localizing specifically at an internal target site, and as a binding agent, for binding the epitopic compound to the target site.

Considering first the binding properties of the protein, it is noted above that the binding protein and the epitope of the epitopic compound are opposite members of a specific, high-affinity binding pair, which may include antigen-antibody, biotin-avidin, and carbohydrate-lectin pairs. In each of these binding pairs, the epitope is a relatively small entity which presents a three-dimensional arrangement of chemical groups, and the binding protein is a relatively large species which has surface features which enable strong non-covalent interaction with the epitope, to bind the two species with a high binding affinity. More generally, the binding protein may contain two or more binding sites and the epitopic compound, two or more epitopes. Preferred binding constants are at least about $10^8 M^{-1}$, and more preferably between about $10^{10}$ and $10^{15} M^{-1}$. A higher binding affinity allows correspondingly less binding protein to be used in practicing the invention, and this can be a significant advantage, particularly where the binding protein is a Mab. For example, if milligram amounts of an antibody with a $10^9$ binding constant are required for efficient compound targeting, microgram and nanogram amounts would be required for achieving the same degree of compound localization using binding proteins with binding affinities of $10^{12}$ and $10^{15}$, respectively.

Monoclonal antibody (Mab) binding proteins can be prepared, by conventional hybridoma techniques, against a large number of haptenic epitopes, and are therefore generally suitable for most chemically modified or derivatized epitopic compounds. To form Mabs against a selected epitope, the epitopic compound, or a related compound containing the epitope, is prepared by standard immunology techniques for injection into an animal, and preferably a mouse, whose lymphocytes can be immortalized by myeloma fusion techniques. Typically, the compound, which itself is rapidly cleared by the kidneys, is covalently conjugated to a large protein or the like, the prevent rapid renal clearance, and mixed with an adjuvant, such as Freund's adjuvant, to enhance the animal's immunological response. The adjuvant mixture is administered by intramuscular or subcutaneous injection, in the usual case, to allow for slow release of the material into the bloodstream. After a two-four week period, spleonocytes are derived from the animal, and these are fused with immortalizing cells, such as mouse myeloma cells, to produce antibody-producing cells capable of long-term growth in culture. The fused cells are selected for those which secrete antibodies specific against the desired epitope. Methods for producing and selecting antibody-producing hybridoma cells are well-known (Kohler). Example 2 details the procedure used to produce Mabs specific against the above thiobutane-BABE-EDTA-Co hapten attached to keyhole limpet hemocyanin as a carrier protein. Three antibody producing cell lines, designated WC3A11, WC4B7, and WC3F5, were selected, and the antibodies from all three lines were specific against both dithiobutane-BABE-EDTA-Co (the Co chelate of compound B in FIG. 1), and In-BLEDTA-IV (the In chelate of compound A in FIG. 1).

The binding data given in Example 2 show that the three anti-thiobutane-BABE-EDTA Mabs described above have binding affinities for selected epitopic metal chelates of between about $1-6 \times 10^9 M^{-1}$. Higher binding affinities may be obtained by one of two general strategies. The first is to select for hybridoma cell lines whose antigen-specific antibodies bind more tightly to the epitope of interest. A second approach is based on the generally higher binding affinities which are observed between an antibody and a bivalent or multivalent antigen. This effect, it should be noted, is not due to simultaneous binding of the two epitopes with the two antibody binding sites, which would be sterically impossible for a small epitopic compound, but appears to be related to the statistically greater opportunity for epitope binding to an antibody where more than one epitope is present.

The extent of binding enhancement seen with bivalent or multivalent epitopic compounds will also depend on the concentration of antibodies which are localized at the target site, in the method of the invention. It is well known that enhanced antigen/antibody binding results if a multivalent antigen can bind simulataneously to two antibodies which are anchored on a surface support. Therefore, assuming an antibody concentration at the target site which would permit such cross-linked antibody binding, delivering a bivalent or multivalent epitopic compound could enhance binding at the target by tenfold or more over that seen for a univalent compound. Methods for preparing mutivalent epitopic compounds are discussed above.

Whereas antibodies offer the advantage that they can be prepared against a wide variety of epitopes, avidin has the advantage of a very high binding affinity (about $10^{15} M^{31\ 1}$) for the epitope biotin. As noted above, this means that the invention can be practiced using much smaller quantities of injected binding protein. Avidin, an egg protein, is commercially available is purified form suitable for use in human therapeutics. Methods for derivatizing chelates and other actice pharmaceutical agents with biotin are discussed above.

Considering the targeting function of the binding protein, the invention relies on the ability of the protein, when administered parenterally, to localize selectively from the bloodstream to the target site. For efficient localization, this requires that the protein (a) have a relatively long circulating half life in the bloodstream, and (b) be capable of accumulate selectively in the target organ. In terms of size requirements, the antibody should be large enough to prevent rapid renal clearance, but not so large as to promote rapid clearance by the RES. Binding proteins, including various types of hybrid proteins discussed below, in the size range between about 50–500,000 daltons are most suitable.

The targeting capability of the binding protein may be based on the ability of the protein to bind specifically to target site antigens, or on protein size or membrane permeability characteristics, or to a combination of these factors. Most target sites, including tumor target sites contain-tissue specific surface antigens against which the binding protein can be directed, and antibodies specific against a variety of normal and malignant tissues have been reported.

It will be recognized that the tissue-specific binding properties of the binding protein are in addition to the binding properties required for binding to the epitopic compound. Therefore it is generally necessary to construct the binding protein to include one or more binding sites against both the tissue antigen and the epitopic compound. Hybrid bivalent antibodies with specificities against two different antigens have been prepared heretofore. In one preparation method, disclosed in U.S. Pat. No. 4,474,893 to Reading, a hybridoma which secretes antibodies specific against one antigen, is fused with a B-lymphocyte or hybridoma capable of secreting antibodies against a second antigen. Some of the trioma or quadroma fusion products are found to secrete a hybrid antibody specific against both antigens. In another approach, the F(ab')$_2$ or Fab fragments produced by enzymatic cleavage of intact antibodies can be chemically linked to one another, or to intact antibodies, to yield an antibody molecule with binding moieties directed against different antigens. Typically in this approach, an intact antibody specific against a target-site antigen is derivatized with Fab or F(ab')$_2$ fragments formed by enzymatic cleavage of an Mab which is specific against the epitopic compound. The coupling may be carried out, for example, by first derivatizing the intact protein with Traut's reagent (see Examples 2 and 3), to attach sulhydryl groups to the protein. The antibody fragments from the epitope-specific proteins are coupled to the sulhydryl groups with a conventional bifunctional reagent having an NHS end groups for coupling with antibody-fragment amines, and an opposite-end maleimide group for coupling to the sulhydryl groups in the derivatized, intact antibody. Other coupling methods known in the art are available.

Alternatively, antibodies or antibody binding fragments can be chemically linked to avidin (or lectin) by analogous coupling methods. Here the antibody fragments in the hybrid protein would function for tissue targeting, while the avidin moiety would provide high affinity binding for biotin-labelled compounds which are targeted to the site.

In one embodiment which is suitable for tumor targeting, selective localization in the tumor is based not on antigen specificity, but on the ability of the protein to penetrate selectively the more permeable, i.e., leaky, capillaries which normally are associated with solid tumors. The advantage of this approach is greater simplicity in preparing the binding protein. Examples 5-6 below illustrate the degree of non-specific tumor localization which can be achieved by this method.

C. Clearing Agent

The clearing agent in the system of the invention functions to bind to and cross-link binding proteins which are circulating in the bloodstream of the treated individual, to promote rapid clearance of the binding protein aggregates by the RES. The agent is preferably large enough to avoid rapid renal clearance, and contains sufficient multivalency to cross-link and aggregate circulating binding proteins. Therefore, the protein preferably has a molecular weight of about 50,000 daltons or more, and is derivatized with the epitopes at a mole ratio of about 1:4 protein:epitope or higher. Here it is noted that protein aggregation by the clearing agent also requires at least two epitope-binding sites on each binding protein.

One preferred clearing agent, for use in humans, is a human protein derivatized with multiple epitopes which are recognized specifically by the binding protein. Example 3 below describes the preparation of a clearing agent consisting of human transferrin derivatized with thiobutane-BABE-EDTA-Co, for cross-linking and clearing Mabs which are specific against compounds of the type shown at A and B in FIG. 1.

II. THERAPEUTIC AND RADIODIAGNOSTIC METHODS

A. Localizing the Binding Protein

The method of the invention is designed for targeting a therapeutic or radiodiagnostic agent to a selected internal body site, such as a tumor region, an internal organ, or some other specific tissue region.

As a first step in the method the binding protein is administered parenterally, i.e., into the bloodstream, preferably by intravenous (IV) administration. From here, the protein slowly passes from the blood, through the extracellular fluid (ECF), and into the body tissues, including the target site, accumulating preferentially in the tumor site because of the targeting feature of the protein. This initial step is illustrated at the top in FIG. 2, which shows slow passage of an antibody binding protein from the bloodstream (dotted-line column) through the ECF into a tumor site.

According to an important advantage of the method, the binding protein is delivered in non-complexed form, i.e., without bound epitopic compound so that the treated individual is not initially exposed to the epitopic compound. The amount of binding protein which is injected is calculated to yield a selected concentration of the epitopic compound at the target site, in the final targeting step. This amount will depend on several factors which include: (a) the relative degree of loaclization of the binding protein in target and non-target regions of the body, (b) the persistence of the binding protein in the blood and, most importantly, (c) the binding constant of the binding protein, when localized at the target site, for the epitopic compound.

The optimal amount of binding protein which is administered can be approximately determined by combining known binding constant data with empirical studies on animal model systems. As a general rule, the amount of binding protein that must be administered to produce a given concentration of targeted compound is inversely related to the protein/compound binding constant. For example, if preliminary animal studies suggest an antibody dose of about 1 mg for an antibody whose binding constant is $10^9 M^{-1}$, the same concentration of would be achieved with an antibody whose binding constant is $10^{12} M^{-1}$, at an antibody dose of 1 $\mu$g. This rule is tempered, in the case of mutivalent epitopic compounds, by the consideration that the binding constant will itself depend on binding protein concentration at the target site, as discussed above.

Studies of this type indicate that effective targeting of a radionuclide bound to an epitopic chelate requires an initial antibody human dose of between about 10-100 mg for an antibody having a binding constant of about $10^9 M^{-1}$ with respect to a monovalent epitopic compound. Comparable radionuclide levels should be achieveable with an avidin binding protein, assuming a binding constant of about $10^{15}$ for a biotinylated metal chelate, at a total dose betweem about 10-100 ng.

The administered binding protein, which has a circulating half life in the blood of one to several days, is allowed to localize in the target organ over period of typically about 1–4 days. During this period the binding protein is slowly taken up from the blood by the target tissue, as well as other tissues. In the case of tumors, binding protein accumulation at the target site is enhanced because of the relatively greater leakiness of the capillaries which supply the tumor. As mentioned earlier, tumor localization can be based solely on preferential antibody leakage into the tumor. This mechanism is illustrated in Example 5, which shows, in Table 2A, antibody uptake values for blood, tumor, and a variety of organs. Here it is seen that the major sites of antibody accumulation, 24 hours after antibody administration, are the blood and tumor, although several organs including lungs and the liver, also shown accumulation of the antibody.

B. Clearing the Binding Agent

In the second step of the method, the circulating antibody is cleared rapidly from the bloodstream, to reduce total blood levels of the protein severalfold, without appreciably effecting the levels of binding protein which have accumulated in the target. This step, which is illustrated in the center frame of FIG. 2, is based on the formation in the bloodstream of aggregates of binding proteins and clearing agent, and rapid clearance of these aggregates by the RES. In the FIGURE, the aggregates formed in the bloodstream are shown being removed by the liver, the principle site of uptake by the RES. Because of its rapid removal, the clearing agent does not accumulate appreciably outside the bloodstream, and therefore has little effect on the disposition of binding protein already localized outside the bloodstream.

The amount of clearing agent which is administered is preferably in a molar ratio of between about 1:5–5:1 with respect to the quantity of antibody calculated to be the bloodstream of the treated individual at the time of the clearing step. As will be seen from the data in Example 5, the amount of antibody retained in the bloodstream after 24 hours is typically between about 15–25% of the total amount administered.

The total time allowed for clearance of the binding protein, i.e., before the epitopic compound is administered, may be as short as 15 minutes, but typically ranges from about 1–4 hours. As will be seen from the data in Example 5, a one-hour clearing step reduced blood levels of antibody, 24 hours after antibody injection, about 25 fold, as measured by the amount of radiolabelled epitopic chelate taken up by the blood before and after the clearing step. At the same time, a greater amount of chelate concentrated in the target tumor tissue in the cleared animal, presumably because of the greater amount of chelate available in free form in the bloodstream. The extent of protein clearance from the bloodstream is similar to that observed earlier by the inventors in using specific antibodies for rapid clearance of circulating tumor imaging proteins from the bloodstream (Goodwin, 1984).

C. Uptake of the Epitopic Compound

In the final targeting step, the epitopic compound is administered parenterally, and preferably intravenously, for selective uptake by the localized binding protein. This step, which is illustrated at the bottom in FIG. 2, involves rapid uptake of the compound by localized antibody, in competition with rapid clearance from the bloodstream by the kidneys.

The amount of epitopic compound which is administered is calculated to produce a desired concentration of compound at the target site shortly after compound injection, usually within 1–4 hours after injection. As with the binding protein, the optimal dosage can be calculated approximately from studies on a model animal system combined with the known binding affinity of the binding protein for the compound.

A number of studies on the tumor localization of epitopic chelate-radionuclide compounds have been carried out in support of the invention. In one such study, detailed in Example 5, the BLEDTA-IV-$^{111}$In compound of FIG. 1A was administered 25 hours after antibody injection, and 1 hour after an antibody clearing step with a human-transferrin Benzyl-EDTA-In clearing agent. The distribution of radiolabel in the blood, tumor, and a variety of other tissues three hours after compound administration, and corresponding tumor/organ radioactivity ratios, are given in Table 2C in Example 5. As seen, levels of radiolabel in the tumor were almost ten times that in the blood, and several times that in the major internal organs, including the kidneys and liver. For comparison, the uptake of compound 23 hours prior after antibody injection, but without an antibody-clearance step, is given in Table 2B in Example 5. As seen here, tumor-to-organ ratios for blood, lungs and kidneys, and other internal organs are generally less than 1.

In another study, detailed in Example 6, the above WC3A11 antibody was administered, followed by a chase after 20 hours with transferrin-labelled TBEDTA-Co. One hour later, TBEDTA-$^{57}$Co was given, and allowed to localize for three hours. Whole-body radioimmaging of the treated animal gave the results seen in FIG. 3A, which shows localization of the label in the kidneys (K), bladder (B) and flank tumor (T). The distribution of the label in the tumor, blood and other tissues three hours after label injection is shown in Table 3 in Example 5. The data there is consistent with that in Table 2A, showing high tumor-to-organ ratios for blood, and other internal organs. The higher levels of radiolabel in the kidneys seen in the present study is due presumably to slower clearance of the radiolabeledded compound from the kidneys.

FIG. 3B shows in the same animal imaged in FIG. 3A, but imaged 24 hours after compound administration. The major difference in the longer-term imaging is an absence of label in the bladder. Good tumor imaging with low background is still achieved.

From the foregoing, it can be appreciated how various objects and features of the invention are met. The method provides selective localization of a therapeutic or radioimaging compound, based on accumulation of a target-specific antibody at the selected target site. This feature allows for improved therapeutic effect with reduced side effects for therapeutic agents, and improved imaging with reduced background levels, particularly background levels due to circulating radionuclide.

Because the localization of the compound occurs shortly after compound injection, e.g., 1–4 hours, radionuclides with half lives of about 1–6 hours can be used for radioimaging. In particular, the method allows both $^{99m}$Tc, whose half life is about 6 hours, and $^{68}$Ga, whose half life is 68 minutes, to be used at relatively low radioactivity levels for radioimaging of tumors or other internal target sites. The particular advantage of $^{68}$Ga as a radioimaging agent is its use in photon emission tomography, an imaging technique that allows quantitation of localized radiolabel and resolution down to 5 mm. Heretofore, the large amount of radionuclide needed for imaging required on on-site cyclotron. With the present invention, the ability to localize large quantities of the radionuclide in an hour or less is compatible with radionuclide amounts which can be produced with a much less expensive $^{68}$Ga generator.

The rapid clearance of non-localized compound by the kidneys means that the toxicity associated with the compound in systemic form can be reduced substantially. In the case of $^{111}$In radioimaging, for example, it has been necessary heretofore to attach the metal to a circulating protein, to achieve high levels of the radionuclide at a localized site. This approach is limited by the amount of protein-conjugated metal which can be safely administered due to high levels of the radionuclide in the bloodstream over a several day period. In the present invention, most of the non-localized radionuclide is cleared in a few hours. This advantage also applies to therapeutic drugs, such as anti-tumor drugs, which must be given in large doses to achieve an effective drug level at the target site. Drug treatment has been limited heretofore, for many anti-tumor drugs, by serious side effects associated with large dose levels. In the present invention, the specific binding of the drug at the target sites, due to the presence there of concentrated binding protein, allows therapeutically effective drug concentrations to be achieved at the tumor site with smaller doses of injected drug.

The following examples illustrate the preparation and use of specific embodiments of the invention, but are in no way intended to limit the scope of the invention.

EXAMPLE 1

Preparation of TBEDTA 1,4-butanedithiol was obtained from Aldrich Chemical Co. (Milwaukee, WI); p-bromoacetomidobenzyl-EDTA (BABE-EDTA) was prepared according to the procedure detailed in DeRiemer (1981). Carrier free $^{111}$InCl$_3$ was obtained from Medi-Physics, and purified as described in DeRiemer (1981).

A tenfold molar excess of 1,4-butanedithiol was combined with BABE-EDTA in a total aqueous volume of 15 ml, and the solution was adjusted to pH 8.2 with NaOH. The reaction was allowed to proceed at room temperature and was monitored by thin layer chromatography. When deveoloped on silica gel plates, using a methanol:aqueous ammonium acetate (1:1) solvent system, the migrated with an $R_f$ of about 0.7.

The reaction mixture was extracted with ether, to remove excess dithiobutane, and the dithiobutane-BABE-EDTA (TBEDTA) product was taken to dryness, and redissolved in a 0.1M acetate buffer.

To form the Co or In metal chelates of TBEDTA, about fifty $\mu$l of the metal ion in 0.01M HCl was added to an equal molar volume of 0.5 mM TBEDTA. After vortexing, the solution was neutralized with NaHCO$_3$. The TBEDTA-In and TBEDTA-Co compounds each showed a single $R_f$ value on TLC.

EXAMPLE 2

Preparation of Anti-TBEDTA-Co Mabs

Keyhole limpet hemocyanin (KLH) was obtained from Calbiochem CO (LaJolla, CA).

The protein was dissolved in phosphate buffer and reacted with a Traut's reagent, 2-iminothiolate, at a molar ratio 1:100 protein:reagent, under standard conditions. Traut's reagent reacts with protein lysine amine groups, to form a 4-carbon amidine which terminates in a sulydryl group. After removal of excess Traut's reagent by molecular sieve chromatography, the protein was reacted with a ten fold molar excess of BABE-EDTA-Co under conditions like those used in Example 1. The derivatized protein product has the form:

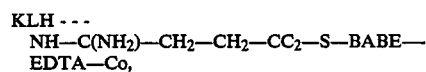

where KLH - - - NH$_2$, is a lysinyl amine of KLH.

The derivatized protein was separated from unreacted TBEDTA-Co by molecular sieve chromatography, concentrated to about 24 mg/ml and mixed with Freund's adjuvant for injection into mice, about 5–10 $\mu$g/animal. Mouse myeloma cells, line P3X63-Ag.8.653 were obtained from the American Type Culture Collection, Rock Lawn, MD, identified as ATCC CRL 1580. Enzyme-labelled goat anti-mouse antibody specific against mouse IgG immunoglobulin was obtained from Sigma Chemical Co. (St. Louis, MO), and subclass specific goat anti-mouse antibodies specific against IgC$_1$, IgG$_{2a}$, IgG$_{2b}$, and IgG$_3$ immunoglubulins were obtained from TAGO, Inc. (Burlingame, CA).

Female Balb/C mice were immunized with the hapten/adjuvant, and about four weeks after immunization, splenocytes derived from the mice were collected, and mixed with the mouse myeloma cells at a cell ratio of 1:2. The cells were washed with RPMI without serum and pelletized. The pellet was gently resuspended in 1 ml of RPMI with 45% (v/v) polyethylene glycol solution, MW 1430–1570 (BDH Chemicals, Poole, England) which was prewarmed to 37 C. After 20 minutes at room temperature, the cell suspension was diluted to 6 ml with RPMI, centrifuged at 500 g for 3 minutes, and beginning at 8 min from the onset of fusion, the cell pellet was washed with 10% FCS.

The fused cells were resuspended in RPMI containing 20% FCS and 100 uM hypoxanthine, 19 uM thymidine (HT medium) and plated in microtiter wells at 10$^5$ cells/well in 60-well trays, a total of 2,000 wells. Cultures were grown in a humidified incubator at 37 C. in 6% CO$_2$. After 24 hours, the medium was changed to the selection medium containing HT medium plus 800 nM aminopterin (HAT medium). The HAT selection medium was used 14 days prior to switch to HT medium, at which point unfused mouse myeloma cells and unfused splenocytes were 100% nonviable.

The cell supernatants from each of the microtitre wells were assayed for anti-TBEDTA-Co antibody by a solid phase enzyme immunoassay. The solid phase assay reagent was prepared by absorbing TBEDTA-Co conjugated to human transferrin (Example 3) to the bottom of microtitre wells in a multiwell plate. In the assay procedure, 50 $\mu$l of supernatant from the individual culture wells were added to a well, and allowed to react with the absorbed antigen for 60 minutes at room temperature. After washing the wells several times with buffer, 50 $\mu$l of enzyme-labelled goat anti-mouse IgG antibody was added, and incubated again for 60 minutes at room temperature. After further washing, the wells were examined for bound enzyme, by a qualitative colorometric determination, according to standard procedures.

Eight wells containing anti-TBEDTA antibody were identified, and three of these parent lines were cloned by limiting dilution in microtitre wells to select clonal antibody producers. The cell supernatants were assayed as above for anti-TBEDTA antibody. A clonal antibody-producing progeny from each of the three parent lines was selected. The three cell lines are identified as WC3A11, WC4B7, and Wc3F5. All three cell lines have shown stable antibody production for several months.

The IgG subclass and antibody binding affinities for TBEDTA-Co, TBEDTA-In (the Co and In chelates, respectively, of compound B in FIG. 1) and BLEDTA-IV-In, (the In chelate of compound A in FIG. 1 are given in Table 1. Antibody subclass for each of the three antibodies was determined by a standard immunodiffusion precipitation method using subclass specific specific goat anti-mouse immunoglobulins. The binding constants of the three monoclonal antibodies were determined by a standard ELISA technique (Friguet). The binding constants are expresses in units of $M^{-1}$. The number in parenthesis below the corresponding binding constant values are percent of whole body retention of radionuclide metal 24 hours after administration of the antibody/chelate complex containing the corresponding Co or In radionuclide.

EXAMPLE 4

Targeting TBEDTA-$^{111}$In to Animal Tumors

EDTA and BABE-EDTA were complexed with $^{111}$In and bleomycin, with $^{57}$Co, as in Example 1. BLEDTA-II-$^{111}$In, a bleomycin-EDTA-In compound which does not contain a dithiobutane linkage between the bleomycin and EDTA moieties, was prepared as described in Goodwin, 1979. BLEDTA-IV-$^{111}$In, a bleomycin-EDTA-In compound containing EDTA linked to bleomycin through a dithiobutane spacer, was prepared as described in co-owned patent application for "Bleomycin Conjugates and Methods". TBEDTA-$^{111}$In was prepared as in Example 1. WC3A11 antibody complexes were formed by incubating the WC3A11 antibody from Example 2 with a selected $^{111}$In cpm amount of (a) $^{111}$-In-EDTA, (b) $^{111}$In-BABE-EDTA, (c) BLEDTA-II-$^{111}$In, (d) BL-$^{57}$Co. (e) BLEDTA-IV-$^{111}$In, or (f) TBEDTA-$^{111}$In.

Each of the antibody/EDTA-$^{111}$In or $^{57}$Co complexes (a)–(f) was subjected intravenously to each of three Balb/C mice, in an amount between about 200–800 μg per animal. Twenty-four hours after the injection, the total body radioactivity of $^{111}$In was measured in a dual-probe scintillation counter. The values were averaged for the three animals. Antibody complexes of compounds (a)–(d) (which do not contain a thiobutane-BABE-EDTA moiety) all showed less than

TABLE 1

| Clone | Ig Subclass | Co—1,4 DT BABE | In—1,4 DT BABE | In—BLEDTA IV |
|---|---|---|---|---|
| WC 3A$_{11}$ | IgG$_3$ | $1.6 \times 10^9$ (70%) | $4.5 \times 10^7$ (31%) | $6 \times 10^9$ $M^{-1}$ (66%) |
| WC 48$_7$ | IgG$_{2a}$ | $1.8 \times 10^9$ | $2.4 \times 10^6$ | $2.8 \times 10^8$ $M^{-1}$ (61%) |
| WC 3F$_5$ | IgG$_{2a}$ | $3.0 \times 10^9$ | $2.9 \times 10^6$ | $1.7 \times 10^8$ $M^{-1}$ (65%) |

% = 24 hours whole body retention using 600 mg WC 3A$_{11}$

The binding data show that all three antibodies have a high affinity for Co-TBEDTA, the hapten used in provoking antibodies in mice. The binding constants for the corresponding In-TBEDTA compounds were much smaller, indicating some metal involvement in antibody specificity. However, the antibodies all reacted strongly with the In-BLEDTA-IV compound, which contains the thiobutane/BABE/EDTA structure in TBEDTA, suggesting that specificity is largely directed to the non-metal portion of the Co-TBEDTA hepten. The binding constant data is consistent with the whole body retention data, which shows (for the WC3A11 antibody which was studied) substantially greater retention of the Co-TBEDTA and In-BLEDTA-IV compounds than the less tightly bound In-TBEDTA compound.

EXAMPLE 3

Preparation of TBEDTA-Derivatized Human Transferrin

Human transferrin was suspended in phosphate buffer and reacted first with about a tenfold excess of Traut's reagent, as in Example 2. After removal of the unreacted Traut's reagent, the derivatized protein was reacted with severalfold excess of BABE-EDTA-Co, as in Example 2, to form a derivatized protein having about 4 moles of attached BABE-EDTA-Co per mole protein. Excess chelate was removed by molecular sieve chromatography and the protein was concentrated.

about 5% whole body retention after 24 hours. By contrast, the antibody complexes of compounds (e) and (f) (both of which contain a thiobutane-BABE-EDTA moiety) were retained to more than 30% after 24 hours, at an initial dose of about 180 μg antibody, and to greater than about 70% of an initial antibody dose of about 800 μg antibody.

EXAMPLE 5

Tumor Targeting of $^{111}$In

This example examines the targeting of $^{111}$In in animal tumors, according to the method of the invention. Balb/C mice were prepared with a KHJJ adenocarcinoma tumor implants in the flank. A hybridoma cell line designated CHA255 specific against L-benzyl-EDTA-In was prepared by methods similar to those described in Example II, using as an immunogen, an L-benzyl-EDTA-In (para-nitrophenolbenzyl-EDTA-In) group derivatized in KLH.

In a first study, a group of three mice were initially injected with 100 ug (about 0.7 nmole) of the CHA255 antibody complexed with L-benzyl-EDTA-$^{111}$In compound. Twenty four hours later, the animals were sacrificed, and examined for $^{111}$In levels in the blood, tumor, and several organs which are listed in Table 3A. The radioactivity levels were calculated in terms of percent of total radioactivity per gram tissue. The average of values obtained for three mice, and standard deviations, are given to the middle column in Table 2A. Tumor/organ (T/O) ratios are shown at the right the the table. As seen, a large percentage of radioactivity remained in the blood, although high amounts were also tumor-localized.

TABLE 2A

| | Hapten-Ab Complex: 24 Hr Conc | |
|---|---|---|
| | %/gm S.D. | T/O Ratio |
| Blood | 13.41 ± 1.48 | 0.8 |
| Heart | 3.23 ± 0.48 | 3.5 |
| Lungs | 6.50 ± 0.91 | 1.7 |
| Liver | 5.76 ± 0.86 | 2.0 |
| Spleen | 2.50 ± 0.37 | 4.5 |
| Kidneys | 3.73 ± 0.81 | 3.1 |
| Tumor | 11.26 ± 1.40 | |
| Muscle | 1.18 ± 0.16 | 9.6 |
| Bone | 1.42 ± 0.22 | 8.0 |
| Skin | 2.35 ± 1.19 | 5.7 |
| Gut | 2.07 ± 1.42 | 7.4 |

In a second study, the antibody alone was administered to each of three animals, and allowed to localize for 23 hours, at which time the L-benzyl-EDTA-$^{111}$In compound was administered. One hour later the animals were sacrificed and again examined for radioactivity levels. Generally, lower levels of tumor uptake and lower tumor/organ uptake ratios, when compared with coadministration of the antibody and In compound (Table 3A) were observed, as seen in Table 2B.

TABLE 2B

| | Ab~23 Hr Prior to Hapten: Conc~1 Hr Post Hapten | |
|---|---|---|
| | %/gm S.D. | T/O Ratio |
| Blood | 24.01 ± 0.80 | 0.17 |
| Heart | 5.40 ± 0.49 | 0.76 |
| Lungs | 9.72 ± 0.24 | 0.42 |
| Liver | 6.35 ± 0.50 | 0.64 |
| Spleen | 3.03 ± 0.27 | 1.36 |
| Kidneys | 5.87 ± 0.81 | 0.70 |
| Tumor | 4.08 ± 0.51 | |
| Muscle | 1.44 ± 0.16 | 2.84 |
| Bone | 1.57 ± 0.09 | 2.59 |
| Skin | 1.60 ± 0.20 | 2.57 |
| Gut | 1.51 ± 0.19 | 2.73 |

A third study examined the degree of tumor localization achievable by an antibody, antibody clearance, and compound administration regimen carried out in accordance with the invention. The CHA255 antibody was administered to each of three animals and allowed to localize for 24 hours, at which time the antibody was cleared from the bloodstream by administration of a clearing agent consisting of transferring derivatized with L-benzyl-EDTA-In. One hour later, the L-benzyl-EDTA-$^{111}$In compound was administered, and the animals sacrificed after an additional three hours. As seen from the data in FIG. 2C, In levels in the blood and internal organs was greatly reduced relative to the levels concentrated in the tumor.

TABLE 2C

| | Ab~25 Hr Prior to Hapten: Conc~3 Hrs Post Hapten (Blocking Agent 1 Hr Prior to Hapten) | |
|---|---|---|
| | %/gm S.D. | T/O Ratio |
| Blood | 0.95 ± 0.44 | 9.20 |
| Heart | 0.92 ± 0.29 | 8.71 |
| Lungs | 2.55 ± 0.24 | 3.02 |
| Liver | 0.87 ± 0.39 | 10.21 |
| Spleen | 0.21 ± 0.04 | 38.03 |
| Kidneys | 1.10 ± 0.16 | 7.04 |
| Tumor | 7.72 ± 1.35 | |
| Muscle | 3.48 ± 0.77 | 2.33 |
| Bone | 1.50 ± 0.37 | 5.40 |

TABLE 2C-continued

| | Ab~25 Hr Prior to Hapten: Conc~3 Hrs Post Hapten (Blocking Agent 1 Hr Prior to Hapten) | |
|---|---|---|
| | %/gm S.D. | T/O Ratio |
| Skin | 4.86 ± 0.45 | 1.61 |
| Gut | 2.66 ± 0.61 | 2.97 |

EXAMPLE 6

Tumor Imaging

Three A Balb/c mice prepared with a KHJJ adenocarcinoma tumor implants in the flank, were administered about 100 μg of WC3A11 antibody (Example 2). Twenty hours after antibody administration, the animals were given a chase of the transferrin/BABE-EDTA-Co clearing agent from Example 3. One hour later (21 hours after antibody administration), the animal received an injection of BLEDTA-IV-$^{111}$In. Three hours later, a whole-body scan, using computer digitation of the whole-body image, was performed on the animals. A representative image obtained for one of the animals in shown in FIG. 3A. The image shows a concentration of radiolabel in the kidneys (K), bladder (B), and the tumor region (T). About 16% of the $^{111}$In administered remained after 3 hours. Two of the animals were sacrificed at this time and examined for $^{111}$In levels in the blood, tumor, and other tissues listed in Table 3 below. As seen from the table, the regimen gave good tumor uptake, and high tumor to blood and low tumor to kidney ratios, consistent with (a) localization of radionuclide in the tumor, and (b) rapid clearance of the radionuclide from the blood by the kidneys.

TABLE 3

| Organ | % Dose Per gm Organ | Tumor/ Organ |
|---|---|---|
| Blood | 0.71 | 5.55 |
| Heart | 0.40 | 9.85 |
| Lungs | 1.01 | 3.91 |
| Liver | 1.24 | 3.20 |
| Spleen | 0.39 | 10.11 |
| Kidneys | 37.78 | 0.11 |
| Tumor | 3.95 | 1.00 |
| Muscle | 0.21 | 18.52 |
| Bone | 1.06 | 3.73 |
| Skin | 0.05 | 4.64 |
| Gut | 1.17 | 3.39 |

A similar whole-body scan was made 24 hours later (48 hours after the antibody administration). The image obtained, shown in FIG. 3B, is similar to the earlier scan, but shows relative absence of label in the bladder. About 14% of the original $^{111}$In material injected was present.

While the invention has been described and illustrated with respect to specific embodiments and features, it will be appreciated that various changes and modifications, particularly with regard to the nature of the epitopic compound and associated binding protein, can be made without departing from the invention.

What is claimed:

1. A method of localizing a diagnostic or therapeutic agent at an internal target site of a subject, said method comprising:
   providing an epitopic compound which is composed of the agent to be targeted and an associated epitopic moiety, and which is rapidly cleared by the kidneys when administered parenterally, providing a binding protein capable of localizing selectively at the target tissue when administered to the subject parenterally, and effective to bind specifically to the epitopic compound at the target site, administering the binding protein parenterally, and allowing the protein to localize selectively at the target site, removing non-localized circulating binding protein by parenterally administering a clearing agent, which clearing agent is different from said epitopic compound, which clearing agent is capable of reacting with circulating binding protein to form a macromolecular aggregate which can be cleared rapidly by the subject's recticuloendothelial system, and after a period sufficient for removal of most of the circulating binding protein, administering the epitopic compound parenterally, whereby binding of the compound to the binding protein localized at the target site and rapid clearance of unbound compound by the kidneys results in selective localization of the compound at the target site.

2. The method of claim 1, wherein the binding protein is avidin and the epitopic moiety is biotin.

3. The method of claim 1, wherein the binding protein is an antibody, and the epitopic moiety is a haptenic moiety which is recognized immunospecifically by the antibody.

4. The method of claim 1, wherein the epitopic compound includes at least two epitopic moieties which are capable of binding to such binding protein.

5. The method of claim 1, for use in targeting the epitopic compound to a target tissue containing target-specific sites, wherein the binding protein contains at least one binding site specific against the epitopic compound, and at least one binding site specific against such target-specific sites.

6. The method of claim 1 for use in targeting the epitopic compound to a target tissue containing target-specific sites, wherein the binding protein is avidin covalently linked to at least one antibody fragment which is specific against such target-specific sites.

7. The method of claim 1, for use in administering the epitopic compound selectively at the site of a solid tumor, wherein the selectivity of binding protein localization is based on selective permeability of the protein across the walls of the capillaries which supply the tumor.

8. The method of claim 7, for localizing a radionuclide at such tumor site, wherein the epitopic compound is a radionuclide metal chelate of a 1-phenyl or 1-benzyl EDTA containing a parasubstituted spacer arm, the binding protein contains at least two binding sites which are specific against the compound, and the clearing agent is a macromolecule containing multiple binding sites which are capable of reacting specifically with the binding protein.

9. The method of claim 1, for use in delivering a radionuclide to the target site, wherein the epitopic compound is a epitope-chelate compound complexed with a metal ion to form a table metal chelate complex.

10. The method of claim 9, wherein the epitope-chelate compound is a metal chelate of a 1-phenyl or 1-benzyl EDTA having a parasubstituted epitope or chemical modification.

11. The method of claim 9, for use in treating a solid tumor, wherein said chelate compound is a metal chelate of $^{90}Y$, $^{197}Hg$ or $^{67}Cu$.

12. The method of claim 9, for use in radioimaging a body tumor, wherein said chelate compound is a metal chelate of $^{111}In$, $^{67}Ga$, $^{64}Cu$, $^{99m}Tc$, $^{68}Ga$, $^{62}Zn$, $^{67}Cu$, $^{197}Hg$, $^{97}Ru$, $^{57}Co$, or $^{53}Co$.

13. The method of claim 9, for use in radiosensitizing a body tumor, wherein said chelate compound is a metal chelate of iron, copper or ruthenium.

14. A system for localizing a a diagnostic or therapeutic agent at an internal target site of a subject, comprising an epitopic compound which is composed of the agent to be localized and an associated epitopic moiety, and which is rapidly cleared by the kidneys when administered parenterally, a binding protein capable of localizing selectively at the target tissue when administered to the subject parenterally, and effective to bind specifically to the epitopic compound at the target site, and a clearing agent capable of reacting with said binding protein, with such circulating in the bloodstream of the subject, to form a macromolecular aggregate which is cleared rapidly by the subject's reticuloendothelial system, wherein said clearing agent is different from said epitopic compound.

15. The system of claim 14, wherein the binding protein is avidin and the epitopic compound includes a biotin epitope.

16. The system of claim 14, wherein the binding protein is an antibody, and the epitopic compound includes a haptenic epitope which is recognized immunospecifically by the antibody.

17. The system of claim 14, wherein the epitopic compound includes at least two epitopes which are capable of binding to such binding proteins.

18. The system of claim 14, for use in delivering a radionuclide to the target site, wherein the epitopic compound is a epitope-chelate compound complexed with a metal ion to form a table metal chelate complex.

19. The system of claim 18, wherein the epitope-chelate compound is a metal chelate of a 1-phenyl or 1-benzyl EDTA.

20. The system of claim 19, wherein the epitope-chelate compound is a metal chelate having thiobutane spacer arm linked to the benzyl moiety.

* * * * *